United States Patent
Colin et al.

(10) Patent No.: US 9,480,428 B2
(45) Date of Patent: Nov. 1, 2016

(54) ASSEMBLY FOR DETERMINING THE PRESENCE OR ABSENCE OF AN ANALYTE IN A BLOOD SAMPLE AND ANALYSIS UNIT COMPRISING SUCH AN ASSEMBLY

(71) Applicant: BIOMERIEUX, Marcy-l'Etoile (FR)

(72) Inventors: Bruno Colin, Marcy l'Etoile (FR); Cécile Paris, Bessenay (FR); Michel Goudard, Saint Genis Les Ollieres (FR)

(73) Assignee: BIOMERIEUX, Marcy-l'Etoile (FR)

( * ) Notice: Subject to any disclaimer, the term of this patent is extended or adjusted under 35 U.S.C. 154(b) by 0 days.

(21) Appl. No.: 14/350,238

(22) PCT Filed: Oct. 3, 2012

(86) PCT No.: PCT/FR2012/052237
§ 371 (c)(1),
(2) Date: Apr. 7, 2014

(87) PCT Pub. No.: WO2013/050701
PCT Pub. Date: Apr. 11, 2013

(65) Prior Publication Data
US 2014/0235970 A1    Aug. 21, 2014

(30) Foreign Application Priority Data
Oct. 5, 2011 (FR) ...................... 11 58998

(51) Int. Cl.
*A61B 5/15* (2006.01)
*A61B 5/151* (2006.01)
(Continued)

(52) U.S. Cl.
CPC .............. *A61B 5/157* (2013.01); *A61B 5/145* (2013.01); *A61B 5/1411* (2013.01); *A61B 5/150022* (2013.01); *A61B 5/15105* (2013.01); *A61B 5/15113* (2013.01); *A61B 5/15117* (2013.01);
(Continued)

(58) Field of Classification Search
None
See application file for complete search history.

(56) References Cited

U.S. PATENT DOCUMENTS 6,016,712 A * 1/2000 Warden .............. G01N 33/4905
73/864.21
2005/0143675 A1 6/2005 Neel et al.
(Continued)

FOREIGN PATENT DOCUMENTS

CN 85 1 04568 A 12/1986
CN 102028478 A 4/2011
(Continued)

OTHER PUBLICATIONS

International Search Report issued in International Patent Application No. PCT/FR2012/052237 dated Jan. 2, 2013.
Jul. 24, 2015 Office Action issued in Chinese Patent Application No. 201210376967.0.

*Primary Examiner* — Erik B Crawford
(74) *Attorney, Agent, or Firm* — Oliff PLC (57) ABSTRACT

This assembly includes: a transportable support; a strip attached to the support and including an application area for applying the sample and at least one reagent required for the analysis; a piercing member for piercing the skin and a blood vessel; and a container for collecting, storing and returning the sample of human or animal blood. The piercing member is inserted into the container. The tip is connected to the support. The container is connected to the support in a removable manner between a storage configuration and a use configuration, in which the container is placed close to the application area.

25 Claims, 4 Drawing Sheets

(51) Int. Cl.
*A61B 5/157* (2006.01)
*G01N 33/558* (2006.01)
*B01L 3/00* (2006.01)
*A61B 5/145* (2006.01)

(52) U.S. Cl.
CPC ..... *A61B 5/15142* (2013.01); *A61B 5/150267* (2013.01); *A61B 5/150305* (2013.01); *A61B 5/150343* (2013.01); *A61B 5/150358* (2013.01); *A61B 5/150412* (2013.01); *A61B 5/150503* (2013.01); *A61B 5/150549* (2013.01); *A61B 5/150618* (2013.01); *A61B 5/150717* (2013.01); *B01L 3/5023* (2013.01); *G01N 33/558* (2013.01); *B01L 2300/0672* (2013.01); *B01L 2300/0816* (2013.01); *B01L 2300/0825* (2013.01); *G01N 2333/16* (2013.01)

(56) References Cited

U.S. PATENT DOCUMENTS

2006/0172435 A1    8/2006  Cho et al.
2007/0239069 A1*  10/2007  Guirguis ............ A61B 10/0051
                                                            600/584
2010/0160831 A1    6/2010  Stout et al.

FOREIGN PATENT DOCUMENTS

EP           1 776 924 A1    4/2007
WO      WO 03/049609 A1      6/2003
WO      WO 2008/075213 A2    6/2008
WO      WO 2009024773 A1 *   2/2009  ............ B01L 3/5023
WO      WO 2010/064998 A1    6/2010

* cited by examiner

ASSEMBLY FOR DETERMINING THE PRESENCE OR ABSENCE OF AN ANALYTE IN A BLOOD SAMPLE AND ANALYSIS UNIT COMPRISING SUCH AN ASSEMBLY

The present invention relates to an assembly for carrying out an assay referred to as rapid test with a view to determining the presence or absence of at least one analyte in a sample of human or animal blood. Furthermore, the present invention relates to an analysis unit comprising such an assembly. The present invention is particularly used in the field of clinical and industrial analyses.

Rapid tests or lateral flow tests are frequently used in the clinical, food, pharmaceutical and chemical fields for determining the presence or absence of various analytes, such as antibodies, antigens, hormones, proteins and chemical molecules in liquid samples, such as blood samples. Rapid tests are commercialized either in the form of simple strips comprising all the physical and biological elements required for the analysis, or in the form of a cassette in which the flow test is included.

By way of example patent application US2006172435A1 describes a rapid test for carrying out an assay with a view to determining the presence or absence of an analyte in a human or animal blood sample. The rapid test of document US2006172435A1 includes a hand transportable casing and a strip which is attached to the casing and which exhibits an application area for applying the blood sample. The strip comprises a reagent suitable for reacting in presence of the analyte, so as to modify the visual aspect of a test area of the strip.

In practice, in order to carry out an assay called rapid test, there are several prior actions to be performed in hygienic and safe conditions: local disinfecting of the collecting area, making available the piercing member kept in sterile conditions, pricking the patient or animal in order to collect the sample to be analyzed, depositing the sample at the analysis strip in an adequate area called application area for applying the sample.

Thus, as described in the aforementioned patent application, the user implements a needle, for piercing the skin and a blood vessel, and a container for storing the blood sample in order to apply it on the application area.

However, the drawbacks pertaining to the practices of the prior art are many:
the user must have:
  the actual rapid test,
  the piercing and collecting members of the sample, and
  the container for collecting the sample,
thus requiring several different packages for each aforementioned member; moreover, each of the aforementioned members must be perfectly calibrated according to the analysis to be carried out, and
in addition, the user must obtain an independent means for locally sterilizing the piercing area of the patient or animal.

Generally, a rapid test of the prior art requires that the user ensures that good hygiene and safety practices are followed. However, in some deficient organizations, precarious economies, etc. . . . , these good practices of hygiene and safety may not be followed, thus leading to significant cross-contamination risks.

The purpose of the present invention is particularly to resolve the aforementioned problems.

To this end, the invention relates to an assembly, for carrying out an assay with a view to determining the presence or absence of at least one analyte in a sample of human or animal blood, the assembly comprising at least:
  a hand transportable support;
  a strip which is attached to the support and which includes an application area for applying the blood sample and at least one reagent required for the analysis;
  a piercing member, such as a tip, preferably sterile, connected to the support and suitable for piercing the skin and a blood vessel; and
  a container calibrated and suitable for collecting, storing and returning the blood sample, the piercing member being inserted either totally or partially into the container, said container being removably connected to the support in such a manner that the container may be alternatively arranged in a storage configuration and in a use configuration in which the container may be placed close to the application area.

In other words, the support, the strip, the piercing member and the container are attached or connected together such as to form an autonomous assembly.

According to an embodiment of the invention, the assembly further comprises a piece of fabric soaked in disinfectant product and which extends over an outer surface of the support, preferably on the surface opposite to the application area, the assembly further comprising a sealed film, detachable and watertight, the film being arranged such as to cover the piece of fabric in the storage configuration.

In a preferential embodiment, the piece of fabric is folded at the outer surface of the support opposite to the application area.

Thus, such a piece of fabric allows the user, before and after the prick, to disinfect the skin at the place of the prick and the tip if need be. In folded position, the piece of fabric represents an insignificant encumbrance.

Thus, such an assembly allows to gather all the components required for the analysis assay, particularly their packaging and transport may be carried out by means of a unique pack. Furthermore, the connection between the piercing member and the support prevents losing the needle and improves the handling of the assembly. Finally, such an assembly allows to meet all hygiene and safety requirements, avoid cross-contamination issues and ensure a blood collecting of which the volume is perfectly calibrated.

In an embodiment of the invention, the sterile piercing member is obtained by overmolding and remains sterile until its use, particularly when the container is not detached from the support. In other words, the piercing member is sterilized during its overmolding, at more than 120° C. or even higher than 150° C., by the plastic material forming the container, that is to say its walls and/or its sub plate.

Thus, the piercing member is sterilized during the manufacture of the assembly, thus avoiding to provide an additional sterilization step.

In the present application, the term "assembly" designates a group of components which are necessary to achieve an assay with a view to determining the presence or absence of at least one analyte in a sample of human or animal blood.

In the present application, the term "connect" and its derivatives designate a material or mechanical, direct or indirect connection between two members. In other words, two members may be mechanically connected together or by means of a third member.

In the present application, the term "piercing member" designates a tip, needle, blade or any other equivalent member suitable for piercing the skin and a blood vessel. In the present application, the term "pierce" and its derivatives designates the actions consisting of perforating or cutting.

In the present application, the term "container" designates a hollow object capable of containing a liquid, for example a blood sample. In other words, the container essentially defines a cavity in which the liquid may be contained.

In the present application, the expression "calibrated and suitable for collecting, storing and returning the sample of human or animal blood" indicates that the user may collect and store a volume of blood adequate and necessary for the analysis by placing the container close to the prick, then return this volume to the application area of the strip.

In the present application, the term "inserted" and its derivatives designates the insertion of the piercing member into the container, that is to say either inside the hollow volume defined by the container, or fitted into the container (that is to say on a sub plate or a wall of this container).

According to an embodiment of the invention, in the storage configuration, the container is attached to the support and the piercing member is attached to the support.

In other words, the container is directly connected to the support and the piercing member is directly connected to the support.

According to another embodiment of the invention, in the storage configuration, the container surrounds all or part of the piercing member, the container being totally or partially inserted into the support.

Thus, such an arrangement allows to achieve a compact assembly in the storage configuration, as the piercing member is housed in the volume of the container.

According to another embodiment of the invention, in the storage configuration, the container is connected to the support by means of a compression means, such as a spring, retained by a blocking means, said compression means also being in connection with the piercing member.

Such a compression means may be formed by an elastic return member, such as a spring. Thus, such a compression means and such a blocking means allow to handle the container easily.

According to an alternative embodiment of the invention, the piercing member is movable between a storage configuration, in which the piercing member is arranged inside the support, and a piercing configuration, in which the piercing member is arranged protruding over an edge of the support.

Thus, such a movable piercing member allows to form a secure and compact assembly, because the piercing member is not arranged protruding over an edge of the support; and because a user is not likely to be pricked unexpectedly.

According to an alternative embodiment, the piercing member is movable between the storage configuration, in which the piercing member is located inside the support, set back in the support or level with an outer surface of the support, and the use configuration in which the piercing member is partially protruding out with respect to an outer surface of the support.

According to another alternative embodiment of the invention, the piercing member is movable between the storage configuration, in which the piercing member is set back inside the support, and the use configuration, in which the piercing member is partially protruding out with respect to the support by release under the action by expansion of a compression member.

Such a compression member may be formed by an elastic return means, such as a spring.

According to an alternative embodiment of the invention, the assembly comprises a control button arranged on the support such as to free the compression member. The control button may for example cooperate by elastically snap-fitting with the compression member.

According to an embodiment of the invention, in the storage configuration, the container is connected to the support by means of the piercing member, the piercing member being attached to the support, the assembly comprising a sub plate which is fitted onto the piercing member, the container being attached onto the sub plate.

Thus, such a sub plate allows to protect a user, for example the medical staff, from an unexpected prick, because the piercing member is fitted onto the sub plate. Moreover, such a sub plate allows the user to easily handle the container.

According to an embodiment of the invention, the sub plate is formed by a cap arranged for blocking an end of the container, the cap being made of a resilient material such as to be able to be fitted onto the piercing member.

Thus, such a cap allows to block the container and rapidly and removably attach the sub plate, hence the container, onto the piercing member.

According to an embodiment of the invention, the support is formed by a casing, such as an essentially parallelepiped cassette, and the strip, preferably porous, is arranged inside the casing, the casing exhibiting at least one aperture to clear the application area and at least one aperture to view the result of the assay at the test area.

Thus, such a casing and such a strip allow to carry out assays for most of the analytes to be sought for.

According to an alternative embodiment of the invention, the casing is formed of two half-shells comprising means for attaching a half-shelf on the other half-shell.

Thus, such a casing allows an easy mounting of the strip in a half-shell and it ensures an effective watertightness of the inner volume where the strip is mounted.

According to an embodiment of the invention, the piercing member is arranged protruding over an edge of the support.

Thus, such an arrangement allows to use the piercing member directly, which avoids handling the assembly in order to bring the piercing member out.

According to an embodiment of the invention, the piercing member is formed of a needle or a blade.

Thus, such a needle allows to perforate the skin and a blood vessel, which can be carried out by a user without qualifications, for example by the person from whom the sample is taken.

According to an embodiment of the invention, the container generally has the shape of a tube, preferably with a circular base.

Thus, such a container is simple to handle and manufacture and is well suited to gather a blood sample.

According to an embodiment of the invention, the container is made from a translucent material, preferably from a transparent material.

Thus, such a container allows to view the volume of blood, hence to collect the required volume.

According to an embodiment of the invention, the container has a volume ranging between 30 microliters and 200 microliters, preferably between 60 microliters and 100 microliters.

Thus, such a volume allows to carry out assays for most of the analytes to be sought for.

According to an alternative embodiment of the invention, the container may comprise a level mark.

Thus, such a mark allows to indicate to the user when the collected volume is sufficient for determining the presence or absence of the analyte.

According to an alternative embodiment of the invention, the assembly further comprises a rigid portion protruding over an edge of the support, such as to allow the detachment from the detachable film.

Such a rigid portion allows to easily detach the detachable film.

Furthermore, the present invention relates to an analysis unit, for carrying out an assay with a view to determining the presence or absence of at least one analyte in a sample of human or animal blood, the analysis unit comprising an assembly according to the invention and a sterile packaging, the assembly being arranged in the sterile packaging.

Figure 1:
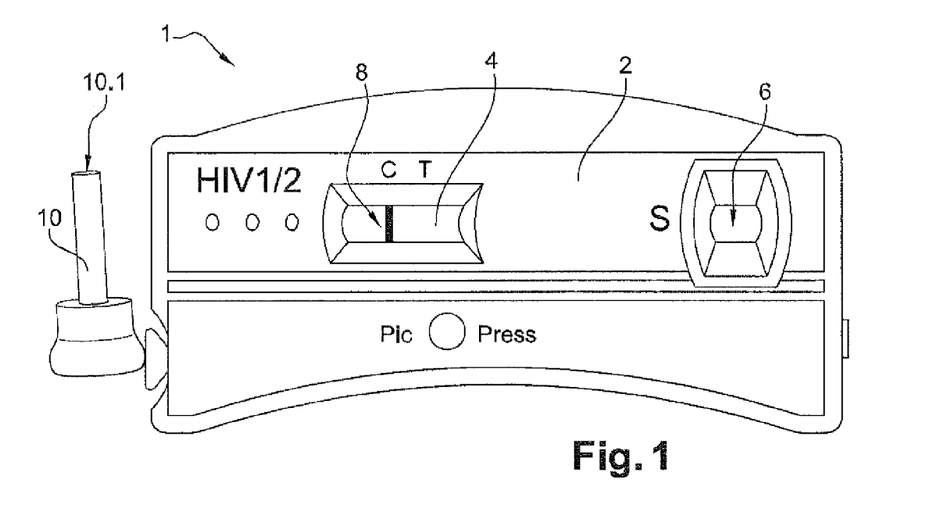
FIG. 1 is a front view of an assembly according to the invention, in storage configuration.
Figure 2:
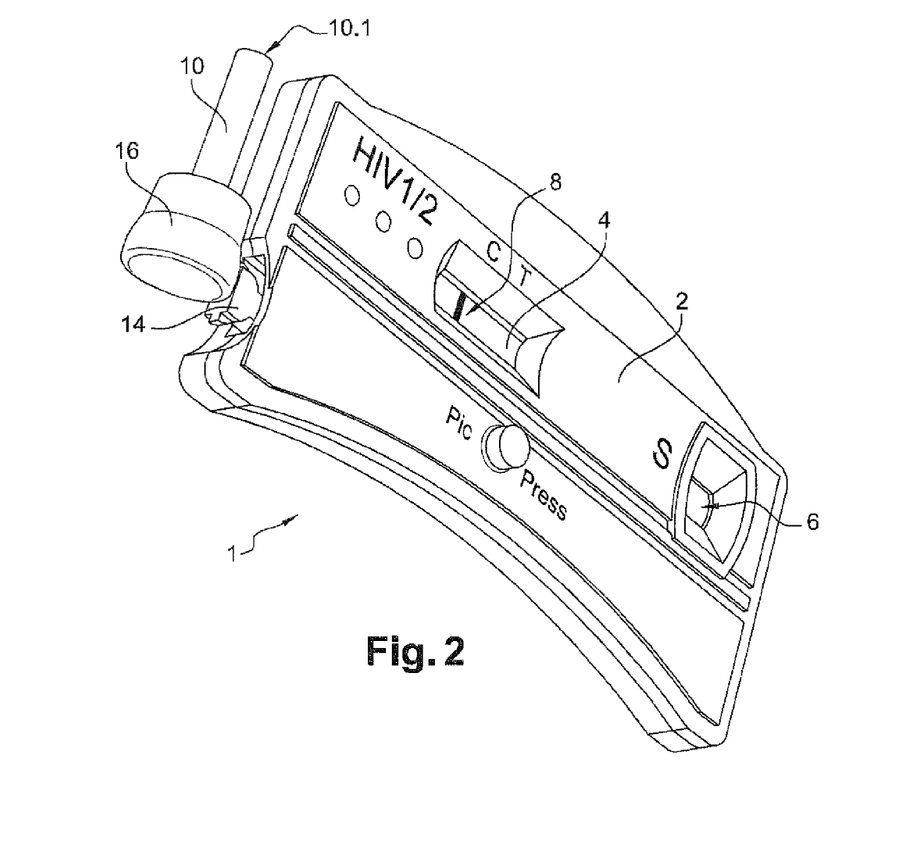
FIG. 2 is a perspective view of the assembly of FIG. 1.

The present invention will be well understood and its advantages will become apparent in light of the following description, given only by way of non limiting example and with reference to the accompanying drawings in which:

FIGS. 1 and 2 illustrate an assembly 1 which has for function, in particular, to allow an assay with a view to determining the presence or absence of at least one analyte in a human or animal blood sample.

The assembly 1 comprises a support which is here defined by a casing 2 which is transportable by hand, for example by a user, as its encumbrance is low. In the example of FIGS. 1 and 2, the casing 2 forms an essentially parallelepiped cassette measuring around 70 mm×35 mm×6 mm.

Furthermore, the assembly 1 comprises a strip 4, for the analysis assay. The strip 4 is attached to the casing 4, as it is described hereinafter in association with FIG. 7. The strip 4 comprises an application area 6 where the blood sample is to be applied. The strip 4 is made from a porous material. The strip 4 further comprises at least one reagent required for the analysis. Such a reagent is suitable for reacting in presence of the analyte, such as to make appear the assay result at a test area 8 of the strip 4.

The assembly 1 further comprises a container 10 calibrated and suitable for collecting, storing and returning the sample of human or animal blood. To this end, the container 10 exhibits an aperture 10.1. Furthermore, the container has a volume of around 75 microliters. In the example of FIGS. 1 and 2, the container 10 has essentially the form of a tube with a circular base. The container 10 is composed of a translucent material, in this instance a transparent material.

Figures 3, 4:
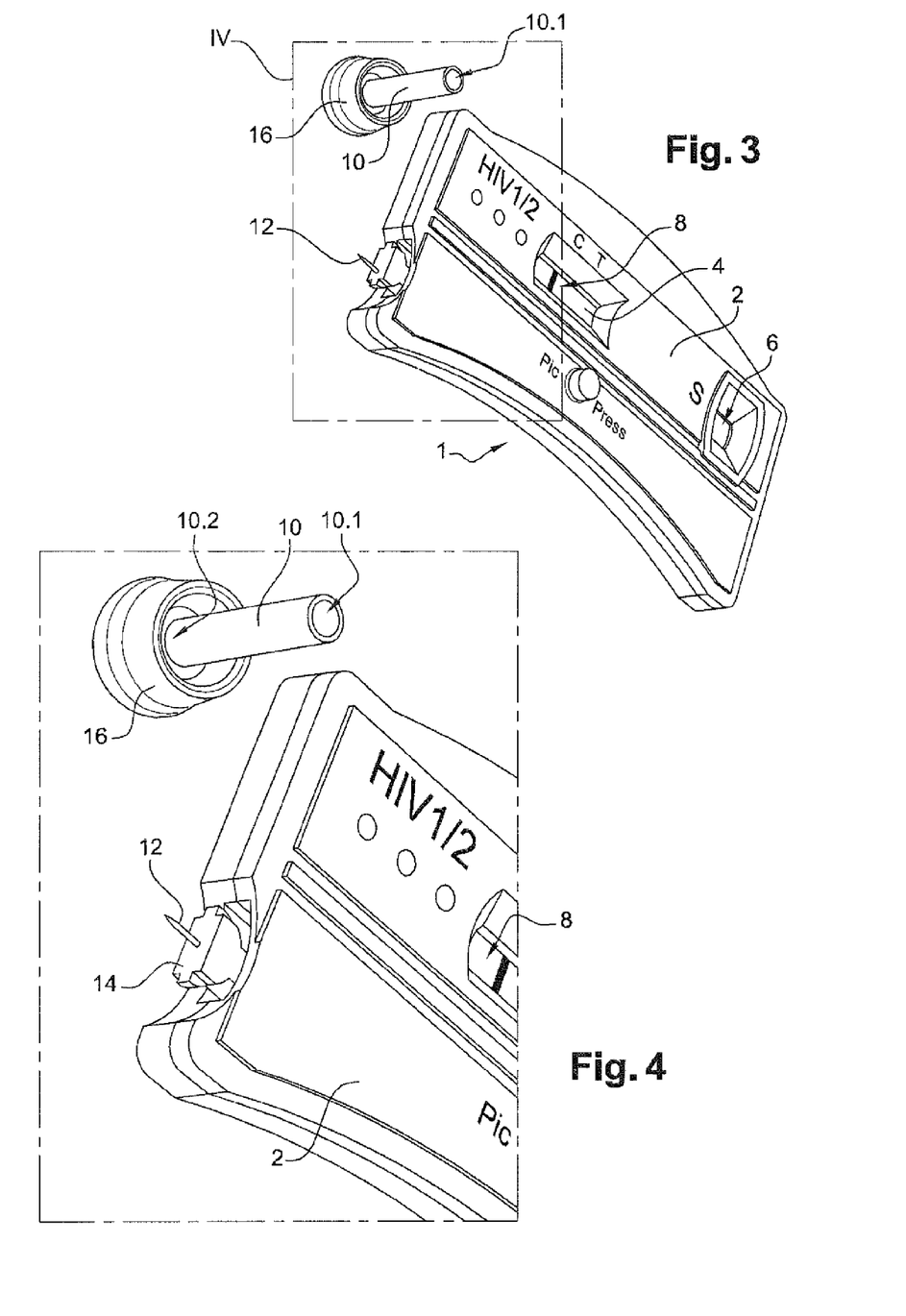
FIG. 3 is a view similar to FIG. 2 of the assembly of FIG. 2 in use configuration.
FIG. 4 is a view of the detail IV of FIG. 3.

As FIGS. 3 and 4 show, the assembly 1 further comprises a piercing member which is here defined by a needle 12 and which is suitable for piercing the skin and a blood vessel. To this end, the needle 12 exhibits a perforating end. The needle 12 may be for example made from a stainless steel.

Furthermore, the container 10 is removably connected to the casing 2 such that the container 10 may be arranged alternatively in a storage configuration (FIGS. 1 and 2) and a use configuration (FIGS. 3 and 4), in which the container 12 may be placed close to the application area 6.

The needle 12 is connected to the casing 2. In the example of FIGS. 3 and 4, the needle 12 is secured to a needle-holder 14 which belongs to the casing 2. The needle 12 is arranged protruding over an edge of the casing 2, in storage configuration (FIGS. 1 and 2) and in use configuration (FIGS. 3 and 4). The needle 12 is stationary or immovable with respect to the casing 2.

In storage configuration (FIGS. 1 and 2), the container 10 is connected to the casing 2 by means of the needle 12. In storage configuration (FIGS. 1 and 2), the container 10 is hence immobile with respect to the casing 2. To this end, the needle 12 is attached to the casing 2. The assembly 1 further comprises a sub plate for indirectly connecting the container 10 to the casing 2. The sub plate here is defined by a cap 16.

The cap 16 is attached to the container 10, for example with glue and the cap 16 is fitted onto the needle 12. Thus, the piercing member 12 is inserted (planted) into the cap 16 which belongs to the container 10.

The cap 16 is arranged in order to block an end 10.2 of the container 10. In the example of FIGS. 1 to 4, the cap 16 is made from a ductile material such that the cap 16 may be fitted onto the needle 12.

Figure 5:
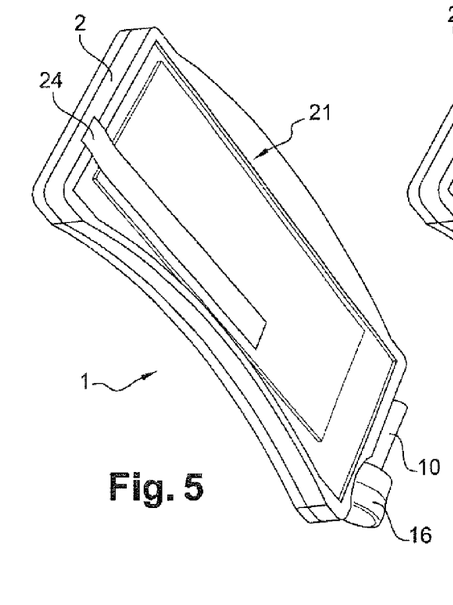
FIG. 5 is a perspective view, according to an angle different from FIG. 2, of the assembly of FIG. 2, in storage configuration.
Figure 6:
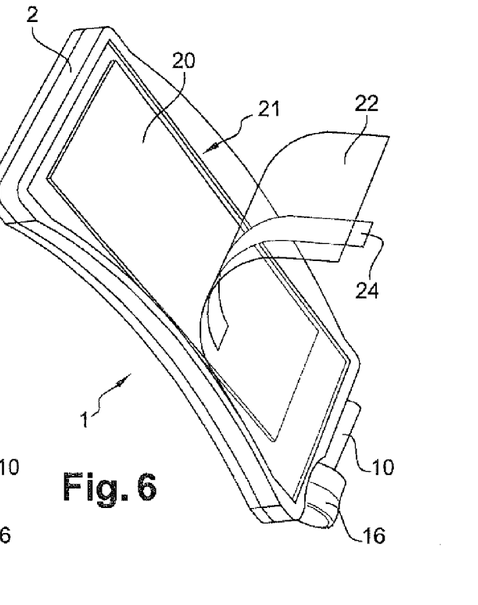
FIG. 6 is a view similar to FIG. 5 of the assembly of FIG. 5, in use configuration.

As FIGS. 5 and 6 show, the assembly 1 further comprises a piece of fabric 20 which is soaked in disinfectant product. The piece of fabric 20 is here formed by a wipe in a non-woven material. The piece of fabric 20 extends on the rear side 21 of the casing 2, that is to say, on the outer surface opposite the application area 6.

As FIG. 6 shows, the assembly 1 further comprises a detachable film 22 which is arranged such as to cover the piece of fabric 20. The detachable film 22 is watertight, particularly to disinfectant product. The detachable film 22 is here made from synthetic plastic material. In the example of FIG. 6, the piece of fabric 20 is folded at the outer surface 21 of the support 2 opposite the application area 6.

Figure 7:
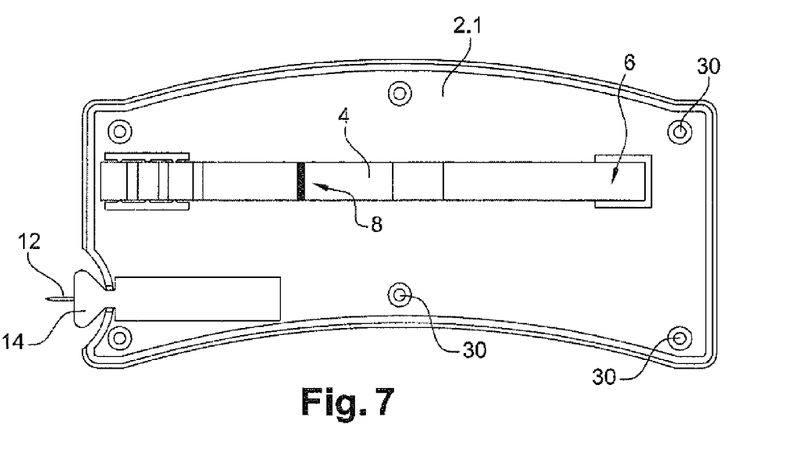
FIG. 7 is a view of a part of the assembly of FIG. 1, in the disassembled state.

As FIG. 7 shows, the strip 4 is arranged inside the casing 2. The casing 2 exhibits an aperture for clearing the application area 6 and an opening for viewing the result of the assay at a test area 8.

The assembly 1 further comprises a rigid portion 24 which protrudes over an edge of the casing 2, such as to allow the detaching of the detachable film 22, hence the clearing of the piece of fabric 20. The rigid portion 24 may be formed by a band in synthetic or metallic material. The rigid portion 24 may be arranged between two strata of the detachable film 22. The rigid portion 24 may advantageously comprise an intelligible indication, written or by ideogram, to indicate to the user how to detach the detachable film 22.

As FIG. 7 shows, the casing 2 is formed of two half-shells, whereof one bears the reference 2.1 in FIG. 7. The half-shells 2.1 and equivalent delimit a hollow volume wherein the strip 4 and a portion of the needle 12 are housed.

Each half-shell 2.1 and equivalent comprises means for attaching a half-shell on the other half-shell, such as to assemble the casing 2. In the example of FIG. 7, the half-shell 2.1 comprises female snap-fitting portions 30 for elastically snap-fitting non represented male portions belonging to the non represented half-shell.

As FIG. 7 shows, the needle 12 is obtained by overmolding and remains sterile until its use, in particular when the container 10 is not detached from the support 2.

In service, a user has a non represented analysis unit in accordance with the invention. The user gets the assembly 1 out from its non represented sterile pack. In order to form an analysis unit in accordance with the invention, the assembly 1 is packed in a sterile environment.

Next, the user pulls the container 10 and the cap 16, such as to remove the needle 12. The user may place the container 10 and the cap 16 on a table beside the casing 2.

Then, the user pulls the rigid portion 24 to totally or partially detach the detachable film 22. The user may reach the thus cleared piece of fabric 20.

The user disinfects the skin at the place of the prick and the needle 12 if need be.

The user pricks the skin and a blood vessel using the needle 12, then collects, in the container 10, an adequate and required volume of blood for the analysis.

Next, the user places the container 10 close to the application area 6 such as to pour thereto the collected blood sample or return it.

Then, the blood sample becomes dispersed or migrates in the strip 4 to the reagent, which reacts if the analyte is present in the dispersed blood sample.

If possible, the user may view the result of the assay at the test area 8, depending on the presence or absence of an analyte in the collected blood sample.

Thus, the user can determine if the test is positive or negative.

Figure 8:
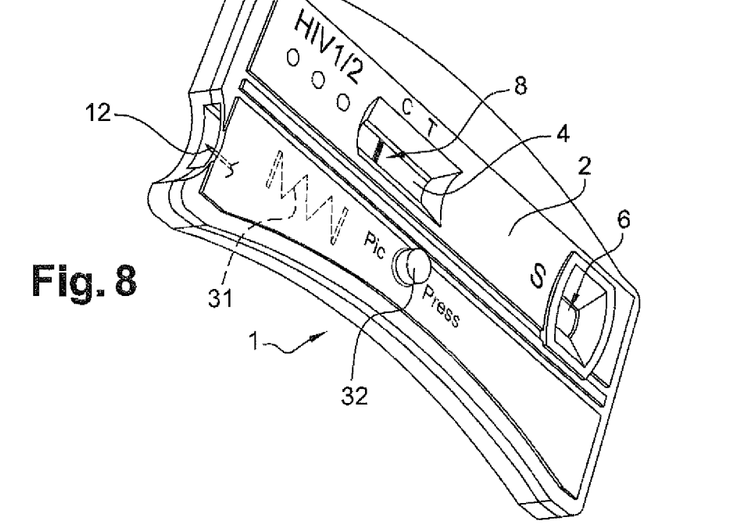
FIG. 8 is a view similar to FIG. 3 of a part of an assembly according to an alternative embodiment of the invention, in storage configuration.
Figure 9:
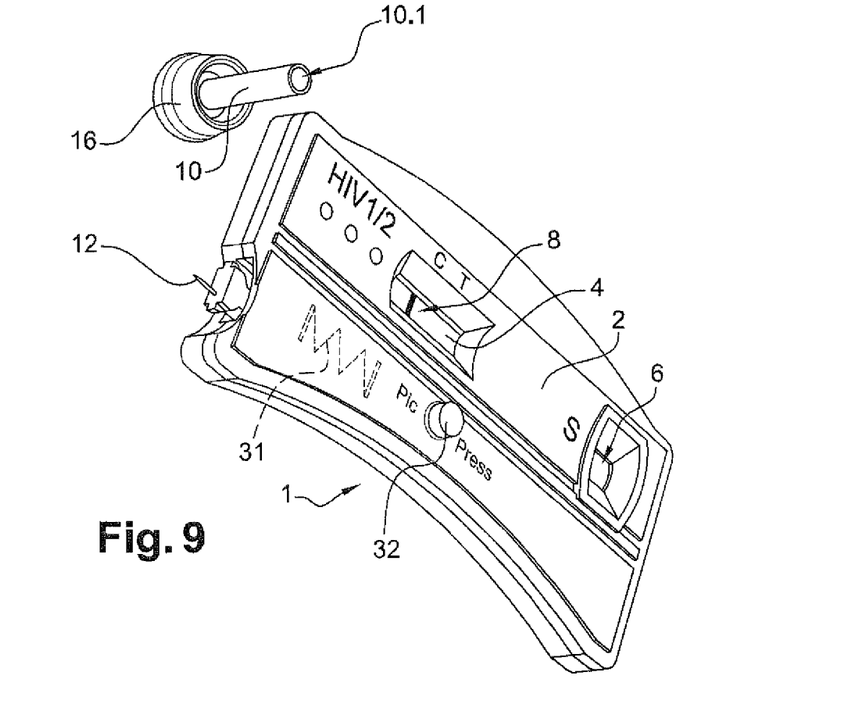
FIG. 9 is a view of the assembly of FIG. 8 in use configuration.

FIGS. 8 and 9 illustrate an assembly 1 in accordance with an alternative embodiment of the invention. In as far as the assembly 1 of FIGS. 8 and 9 is similar to the assembly 1 of FIGS. 1 to 7, the description of the aforementioned assembly 1 in association with the FIGS. 1 to 7 may be transposed to the assembly 1 of FIGS. 8 and 9, except for the noticeable differences mentioned hereinafter.

The assembly 1 differs from the assembly 1, in particular, as in the assembly 1, the piercing member 12 is movable between the storage configuration (FIG. 8), in which the piercing member 12 is located inside the support 2, and the use configuration (FIG. 9), in which the piercing member 12 is partially brought out protruding with respect to an outer surface of the support 2. In the example of FIGS. 8 and 9, the piercing member 12 is arranged level with an outer surface of the support 2.

In addition, the assembly 1 differs from the assembly 1, as to move the piercing member 12 between the storage configuration (FIG. 8) and the use configuration (FIG. 9), the assembly 1 further comprises an elastic return member in compression, here symbolized by a helical spring 31, whereof the expansion releases the piercing member 12.

Furthermore, the assembly 1 comprises a control button 32 which is arranged on the support 2 such as to release the compression member (helical spring 31). The control button 32 cooperates for example by elastically snap-fitting with the compression member (helical spring 31).

In storage configuration, such as in the example of FIGS. 1 to 7, the container 10 is connected to the support by means of the piercing member 12, the piercing member 12 being slidingly connected to the support 2, the assembly 1 comprising a sub plate (cap 16) which is fitted, by overmolding, onto the piercing member 12, the container 10 being attached onto the sub plate (cap 16).

When the user presses the control button 32, the elastic snap-fitting releases the helical spring 31, which allows to move the piercing member 12 towards the use configuration (FIG. 9).

According to other advantageous but optional features, taken alone or according to any technically possible combination:

The container is attached to the support and the piercing member is attached to the support, thus making a direct connection between the container and the support, alternatively to the indirect connection between the container 10 and the aforementioned casing 2.

In storage configuration, the container may surround all or part of the piercing member, the container being totally or partially inserted in the support.

The invention claimed is:

1. An assembly for assaying the presence or absence of at least one analyte in a sample of human or animal blood obtained by piercing skin or a blood vessel of the human or animal, the assembly comprising at least:
   a hand transportable support;
   a strip which is attached to the support and which includes an application area for applying the blood sample and at least one reagent required for a blood analysis;
   a container configured to collect, store and provide the blood sample to the strip, said container being removably connected to the support in such a manner that the container may be alternatively arranged either in a storage configuration or in a use configuration in which the container may be placed close to the application area; and
   a piercing member configured to pierce the skin or the blood vessel, the piercing member being inserted either totally or partially into the container and the piercing member being non-removably attached to the support while in use.

2. The assembly according to claim 1, further comprising:
   a piece of fabric which is soaked in disinfectant product and which extends over an outer surface of the support; and
   a sealed film, detachable and watertight, the film being arranged such as to cover the piece of fabric when the container is arranged in the storage configuration.

3. The assembly according to claim 1, configured such that when the container is arranged in the storage configuration, the container and the piercing member are each attached to the support.

4. The assembly according to claim 3, configured such that when the container is arranged in the storage configuration, the piercing member is either totally or partially housed within a hollow volume of the container in which the sample may be contained, and the container is either totally or partially inserted into the support.

5. The assembly according to claim 1, configured such that when the container is arranged in the storage configuration, the container is connected to the support by a compression means, said compression means also being in connection with the piercing member.

6. The assembly according to claim 1, further comprising a sub plate which is fitted onto the piercing member, the container being attached onto the sub plate,
   wherein the assembly is configured such that when the container is arranged in the storage configuration, the container is connected to the support by means of the piercing member.

7. The assembly according to claim 6, wherein the sub plate is formed by a cap arranged for blocking an end of the container, the cap being made of a resilient material so as to be able to be fitted onto the piercing member.

8. The assembly according to claim 1, wherein:
   the support is formed by a casing, the casing exhibiting at least one aperture to clear the application area and at least one aperture to view the result of the assay at a test area; and the strip is arranged inside the casing.

9. The assembly according to claim 1, wherein the piercing member is arranged protruding over an edge of the support.

10. The assembly according to claim 1, wherein the piercing member is formed of a needle or a blade.

11. The assembly according to claim 1, wherein the container has essentially the form of a tube.

12. The assembly according to claim 1, wherein the container is made of a translucent material.

13. The assembly according to claim 1, wherein the container has a volume ranging between 30 microliters and 200 microliters.

14. An analysis unit comprising:

a sterile packaging, and the assembly according to claim 1, the assembly being arranged in the sterile packaging.

15. The assembly according to claim 2, wherein the outer surface of the support is a surface opposite to the application area.

16. The assembly according to claim 5, wherein the compression means is a spring.

17. The assembly according to claim 8, wherein the casing is an essentially parallelepiped cassette.

18. The assembly according to claim 8, wherein the strip is porous.

19. The assembly according to claim 12, wherein the container is made of a transparent material.

20. The assembly according to claim 13, wherein the container has a volume ranging between 60 microliters and 100 microliters.

21. The assembly according to claim 15, wherein the piece of fabric is folded at the outer surface of the support opposite to the application area.

22. An assay method that uses the assembly according to claim 1, the method comprising at least:

removing the container from the support so that the container is in the use configuration;

piercing skin or a blood vessel of a human or animal using the piercing member to obtain a blood sample;

collecting the blood sample in the container;

providing the blood sample from the container to the application area of the strip; and assaying for the presence or absence of at least one analyte in the blood sample.

23. An assembly for assaying the presence or absence of at least one analyte in a sample of human or animal blood obtained by piercing skin or a blood vessel of the human or animal, the assembly comprising at least:

a hand transportable support;

a strip which is attached to the support and which includes an application area for applying the blood sample and at least one reagent required for a blood analysis;

a container configured to collect, store and provide the blood sample to the strip, said container being removably connected to the support in such a manner that the container may be alternatively arranged either in a storage configuration or in a use configuration in which the container may be placed close to the application area;

a piercing member configured to pierce the skin or the blood vessel, the piercing member being inserted either totally or partially into the container;

a piece of fabric which is soaked in disinfectant product and which extends over an outer surface of the support; and a sealed film, detachable and watertight, the film being arranged such as to cover the piece of fabric when the container is arranged in the storage configuration.

24. An assembly for assaying the presence or absence of at least one analyte in a sample of human or animal blood obtained by piercing skin or a blood vessel of the human or animal, the assembly comprising at least:

a hand transportable support;

a strip which is attached to the support and which includes an application area for applying the blood sample and at least one reagent required for a blood analysis;

a container configured to collect, store and provide the blood sample to the strip, said container being removably connected to the support in such a manner that the container may be alternatively arranged either in a storage configuration or in a use configuration in which the container may be placed close to the application area; and a piercing member configured to pierce the skin or the blood vessel, the piercing member being non-removably attached to the support while in use.

25. An assay method that uses the assembly according to claim 24, the method comprising at least:

removing the container from the support so that the container is in the use configuration;

piercing skin or a blood vessel of a human or animal using the piercing member to obtain a blood sample;

collecting the blood sample in the container;

providing the blood sample from the container to the application area of the strip; and assaying for the presence or absence of at least one analyte in the blood sample.

* * * * *